United States Patent
Arizti et al.

(10) Patent No.: US 8,277,431 B2
(45) Date of Patent: Oct. 2, 2012

(54) ABSORBENT ARTICLE WITH MULTIPLE ELASTIC AREAS

(75) Inventors: Blanca Arizti, Frankfurt (DE); Darrell Ian Brown, Mason, OH (US); Cornelia Beate Martynus, Schwalbach (DE); Ekaterina Anatolyevka Ponomarenko, Mechernich Floisdorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 335 days.

(21) Appl. No.: 12/697,335

(22) Filed: Feb. 1, 2010

(65) Prior Publication Data

US 2010/0198180 A1    Aug. 5, 2010

Related U.S. Application Data

(60) Provisional application No. 61/149,075, filed on Feb. 2, 2009.

(51) Int. Cl.
*A61F 13/15* (2006.01)

(52) U.S. Cl. ......... 604/385.24; 604/385.25; 604/385.26; 604/385.29

(58) Field of Classification Search ............. 604/385.24, 604/385.25, 385.26, 385.29
See application file for complete search history.

(56) References Cited

U.S. PATENT DOCUMENTS

| | | | |
|---|---|---|---|
| 3,860,003 A | 1/1975 | Buell | |
| 4,695,278 A | 9/1987 | Lawson | |
| 4,795,454 A | 1/1989 | Dragoo | |
| 4,808,178 A | 2/1989 | Aziz et al. | |
| 5,518,801 A | 5/1996 | Chappell et al. | |
| 5,571,096 A | 11/1996 | Dobrin et al. | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,865,823 A | 2/1999 | Curro | |
| 5,938,648 A | 8/1999 | LaVon et al. | |
| 5,947,947 A | 9/1999 | Tanzer et al. | |
| 2005/0273071 A1 | 12/2005 | McKiernan et al. | |
| 2006/0058765 A1 | 3/2006 | Mueller et al. | |
| 2007/0088302 A1 | 4/2007 | Sugiyama et al. | |
| 2007/0191806 A1 | 8/2007 | Mueller et al. | |

FOREIGN PATENT DOCUMENTS

| | | |
|---|---|---|
| EP | 0 626 160 A1 | 11/1994 |
| EP | 0357298 B1 | 11/1994 |
| WO | WO 95/16746 | 6/1995 |
| WO | WO 95/24173 | 9/1995 |
| WO | WO 03/009795 | 2/2003 |
| WO | WO 2006/031642 | 3/2006 |

OTHER PUBLICATIONS

International Search Report, dtd Apr. 22, 2010, 7 pages.

*Primary Examiner* — Jacqueline F. Stephens
(74) *Attorney, Agent, or Firm* — Abbey A. Lopez; Charles R. Matson (57) ABSTRACT

An absorbent articles, such as diapers, training pants, adult incontinence articles, feminine protection articles and the like having a specific elasticated topsheet comprising multitude of elasticated areas and one or more openings to receive e.g. feces, the elasticated areas being typically straight, but the elasticated areas operating jointly to provide a diverting-like elastic behavior, and the elasticated areas having optionally different elastic properties.

13 Claims, 4 Drawing Sheets

000
ABSORBENT ARTICLE WITH MULTIPLE ELASTIC AREAS

CROSS REFERENCE TO RELATED APPLICATIONS

This application claims the benefit of U.S. Provisional Application No. 61/149,075 filed on Feb. 2, 2009, which is herein incorporated by reference in its entirety.

FIELD OF THE INVENTION

The present disclosure is directed to absorbent articles, such as diapers, training pants, adult incontinence articles, feminine protection articles and the like having a specific elasticated topsheet comprising multitude of elasticated areas.

BACKGROUND OF THE INVENTION

A well-known problem with diapers is that feces, and in particular runny feces, may leak out of the diaper in use. A range of solutions has been suggested to better store feces in the diaper, including diapers with a topsheet with one or more openings, through which the feces can pass to a void space between the topsheet and the absorbent core. The problem with such diapers is that the opening is difficult to position correctly in use, such that the feces will actually pass through the opening, and such that the opening does not close in use, in particular when the user (baby) moves around.

Hereto, diapers have been developed that comprise at least one aperture in the topsheet and front and rear portion elastic contracting strands which provide an alignment of the aperture relative to the anal opening, as disclosed in EP 0 357 298 B1.

As disclosed in WO 03/009795, diapers comprising a slit opening and longitudinally opposing side edges, each having a diverting elasticated region disposed along each of the side edges have been developed. These diapers are such that the correct alignment is achieved when the article is first applied, independent on whether the article is applied correctly, and such that the correct alignment is remained in use.

As disclosed in WO 2006/031642, such diapers with openings can be improved by providing the topsheet with specific additional, curved secondary elastics, which are such that also an improved cross-machine direction force is obtained, mainly in the crotch portion of the diaper, which ensures that the opening remains open in use and does not slip into the anus and which ensures that the opening remains aligned with the gluteal groove and close enough to the anus.

However it is not easy to process such diapers with diverting or curved elastics at high speed. Furthermore, it would be desirable to find a way to provide such diapers with elasticated areas allowing more design flexibility.

A way to solve this problem is described herein, by providing a topsheet with one or more opening with separated elasticated areas in the crotch portion and in the front and/or back portion, wherein the elasticated areas operated together to provide an elasticated topsheet with diverting-like elasticity, that ensures correct positioning or alignment of the opening(s) prior to use and during use, whilst being easily applicable to the topsheet at high speed, the elasticated area in the front and/or back and in the crotch portion being typically straight and placed under an angle with one another. Furthermore, the elasticated areas may be made of different elastic material so that different elastic properties or profiles can be obtained in different areas of the topsheet, in an easy manner.

SUMMARY OF THE INVENTION

In a first embodiment, a disposable absorbent article (10) having a backsheet, a topsheet (11) and an absorbent core (12), the absorbent core (12) being positioned between the topsheet (11) and the backsheet, the topsheet (11) comprises:
a) a pair of opposing first (21) and second (22) longitudinal side edges;
b) a longitudinal axis (Y) and a transverse axis (X), perpendicular to the longitudinal axis (Y);
c) a first longitudinal side (23), positioned from the longitudinal axis (Y) to a first longitudinal side edge (21) of the topsheet comprising a first front portion (25a), a first back portion (27a) and a first crotch portion (26a) positioned between the first front portion (25a) and the first back portion (27a) and a second longitudinal side (24) positioned from the longitudinal axis (Y) to the opposite, second longitudinal side edge (22) of the topsheet comprising a second front portion (25b), a second back portion (27b) and a second crotch portion (26b) positioned between the second front portion (25b) and the second back portion (27b);
d) one or more openings (13), each opening having first and second, opposing, longitudinal side edges (14), and providing a passageway to a void space (15) for receiving bodily exudates therein, the void space (15) being positioned between the topsheet (11) and the absorbent core (12),
whereby the topsheet (11) comprises:
i) in at least part of the first crotch portion (26a), at least a first primary elasticated area (31) and in at least part of the second crotch portion (26b), at least a second primary elasticated area (32) having each a primary direction of stretch D1 substantially parallel to the longitudinal axis of the topsheet (Y); and
ii) in at least part of the first front portion (25a), at least a first secondary elasticated area (33) and in at least part of the second front portion (25b), at least a second secondary elasticated area (34), the first secondary elasticated area (33) having a direction of stretch $D2_1$, having an angle $\alpha 2_1$ of 10 to 60° with a parallel line of D1 and the second secondary elasticated area (34) having a direction of stretch $D2_2$, having an angle $\alpha 2_2$ of −10° to −60° with a parallel line of D1; and/or
iii) in at least part of the first back portion (27a), at least a first tertiary elasticated area (35) and in at least part of the second back portion (27b) at least a second tertiary elasticated area (36), the first tertiary elasticated area (35) having a direction of stretch $D3_1$, having an angle $\alpha 3_1$ of −10 to −60° with a parallel line of D1 and the second tertiary elasticated area (36) having a direction of stretch $D3_2$, having an angle $\alpha 3_2$ of 10° to 60° with a parallel line of D1.

In one embodiment, the primary, the secondary and/or the tertiary elasticated areas are each straight. Such straight elastic areas are easy to process and can be provided such that an absorbent article with diverting-like elasticated areas and diverting-like elastic behavior is obtained without using a complex elastic-diverting process step.

In one embodiment described in more detail below, the elasticated areas are formed by first joining or attaching two or more, typically straight and optionally different, elastic materials to one another under an angle, e.g. those forming the first primary, secondary and/or tertiary areas, and then attaching the thus attached elastic materials to the topsheet material, (and in such a case, the transverse edges of a first primary and a first secondary and/or the transverse edges of a first primary and a first secondary elasticated area are thus in contact with one another).

DETAILED DESCRIPTION OF THE INVENTION

As used herein, 'absorbent article' means any article that can absorb body fluids and is suitable to be placed in close proximity to the genitals of the user, including in particular an adult or infant diaper including so-called training pants.

As used herein, 'longitudinal' is the direction running substantially parallel to the maximum linear dimension of the topsheet or article, typically to the longitudinal axis of the topsheet, and includes directions within 20° of this parallel.

The 'lateral' or 'transverse' direction is orthogonal to the longitudinal direction, typically parallel to the transverse axis and in the same plan of the majority of the article and the longitudinal axis, and includes directions within 20° of the orthogonal.

As used herein, 'first longitudinal side' refers to the region of the topsheet which is positioned from the longitudinal axis of the topsheet to a first longitudinal side edge of the topsheet.

As used herein, 'second longitudinal side' refers to the region of the topsheet which is positioned from the longitudinal axis of the topsheet to a second longitudinal side edge of the topsheet.

As used herein 'front portion' and 'back portion' refer to the two regions of the topsheet or article, which are in use, respectively, closest to the front of the wearer and the back of the wearer and whose length is approximately one third of the length of the topsheet or article and whose width is equal to the width of the topsheet or article.

As used herein 'crotch portion' refers to the region of the topsheet or article positioned in the center of the topsheet or article between the front and the back portion of the topsheet or article and whose length is approximately one third of the length of the topsheet or article and whose width is equal to the width of the topsheet or article.

As used herein, 'opening in the topsheet' means an area circumscribed by the topsheet, but where the topsheet material is not present, and which is large enough to receive fecal material, typically being at least 2 cm long or wide, or having a surface area of at least 2 $cm^2$.

As used herein, the term 'void space' is a cavity in the article present in at least the relaxed state, accessible via an opening(s) in the topsheet, and which serves to accept and contain bodily exudates such as fecal material, typically being at least 5 $cm^3$ in relaxed state.

As used herein, 'elasticated' and 'elasticated area' mean that the topsheet or topsheet material comprises at least a portion that is elastic, being made of or comprising an elastic material.

As used herein, 'direction of stretch' is the direction in which the elastics bands or strands comprising by the topsheet are elastically stretchable.

As used herein, 'direction parallel to the longitudinal axis' includes direction within 20° of this parallel, when applicable.

As used herein 'stretched' or 'stretched state' means that the article or topsheet thereof is stretched to its maximum length, which is typically determined by the length of a non-extendable or non-elastically extendable component which is part thereof, e.g. the backsheet or the topsheet material.

A non-elastically extendable material or component as used herein may be stretched or extended to a maximum stretched or extended length, which is at least 120% of its original length, by a stretching force (without rupturing or tearing), but its relaxed length, upon release of the force, is at least 50% of the maximum stretched or extended length (after 5 minutes of release of the force and at 25° C.).

As used herein 'relaxed' or 'relaxed state' means the state that no forces are applied to the article or topsheet (other than naturally occurring forces such as gravity), when the article is laid on a horizontal surface, such that the transverse front and back edge are flat on the horizontal surface and the transverse centre line or axis is on the horizontal surface.

As used herein, the term 'attached' encompasses configurations whereby a first element is directly secured to another element by affixing the first element directly to a second element and whereby a first element is indirectly secured to a second element by affixing the first element to a third, intermediate member(s), which in turn are affixed to the second element.

As used herein, the term 'elasticity' is the ability of the article or the topsheet or an elastic area with an original relaxed length to be stretched by a force to a stretched state with a stretched length which is at least 150% of its original relaxed length without tearing or rupturing and, after being stretched to this stretched state, to return to a relaxed state upon release of the stretching force, wherein it has recovers to 95% to 120% of its original relaxed length within 5 minutes of removal of the stretching force at 25° C.

Figure 1:
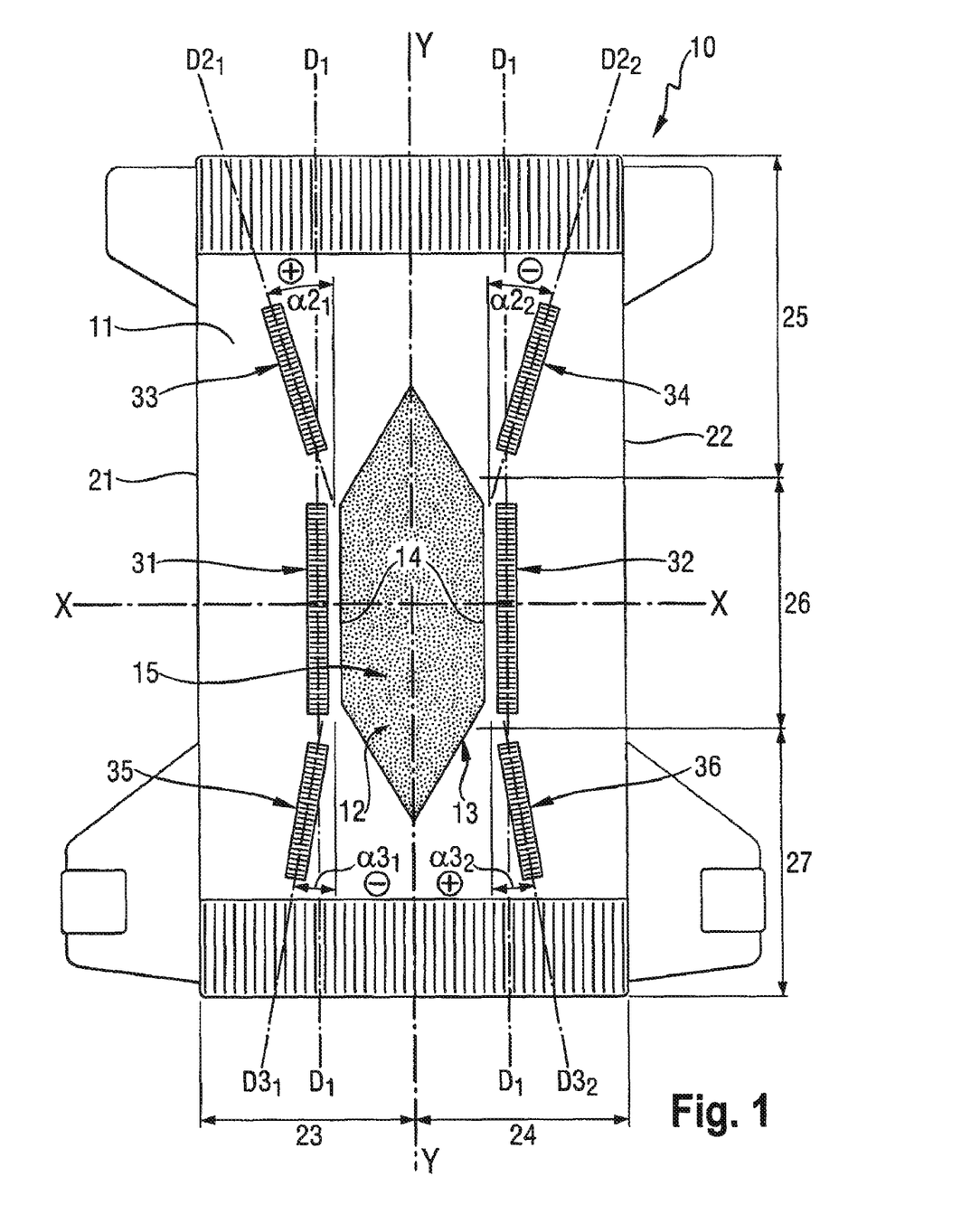
FIG. 1 shows a plan view of a disposable absorbent article configuration.

The absorbent article (10) comprises a topsheet comprising a pair of opposing first (21) and second (22) longitudinal side edges as for example shown in FIG. 1. The topsheet (11) of the absorbent article (10) comprises a longitudinal axis (Y) and a transverse axis (X), perpendicular to the longitudinal axis (Y).

The topsheet (11) of the absorbent article (10) comprises one or more openings (13). The dimensions and exact shape of the opening(s) (13) may vary, depending on the size of the topsheet (11) and/or the absorbent article (10).

In one embodiment, the absorbent article comprises a single opening for the reception of bodily exudates. The opening may be present in at least part of the crotch portion of the topsheet, and extends optionally into part of the front portion (in use towards the front of the user) and/or into part of the back portion (in use towards the back of the user) of the topsheet. The opening may be in the form of a longitudinally extending opening, or for example a so-called slit opening, with substantially parallel longitudinal side edges which typically has a longitudinal dimension (length) substantially parallel to the longitudinal axis of the topsheet and of the absorbent article. In one embodiment, the slit opening is such that in stretched state its length is much longer than its width, namely having a ratio of at least 7:1, or at least 10:1, and may be up to 40:1, or 30:1.

In one (other) embodiment, the slit opening herein is an opening that may be made by cutting a slit through the topsheet or topsheet material, the slit cut having no width dimension.

In stretched state, the opening of the topsheet may be configured such that from 20% to 40%, or may be from 20% to 30% of the length of the opening extends from the transverse axis (X) of the topsheet towards the front edge of the topsheet (i.e. present in the front portion) and the remaining percentage extends towards the back edge of the topsheet (i.e. present in the back portion).

Figure 3:
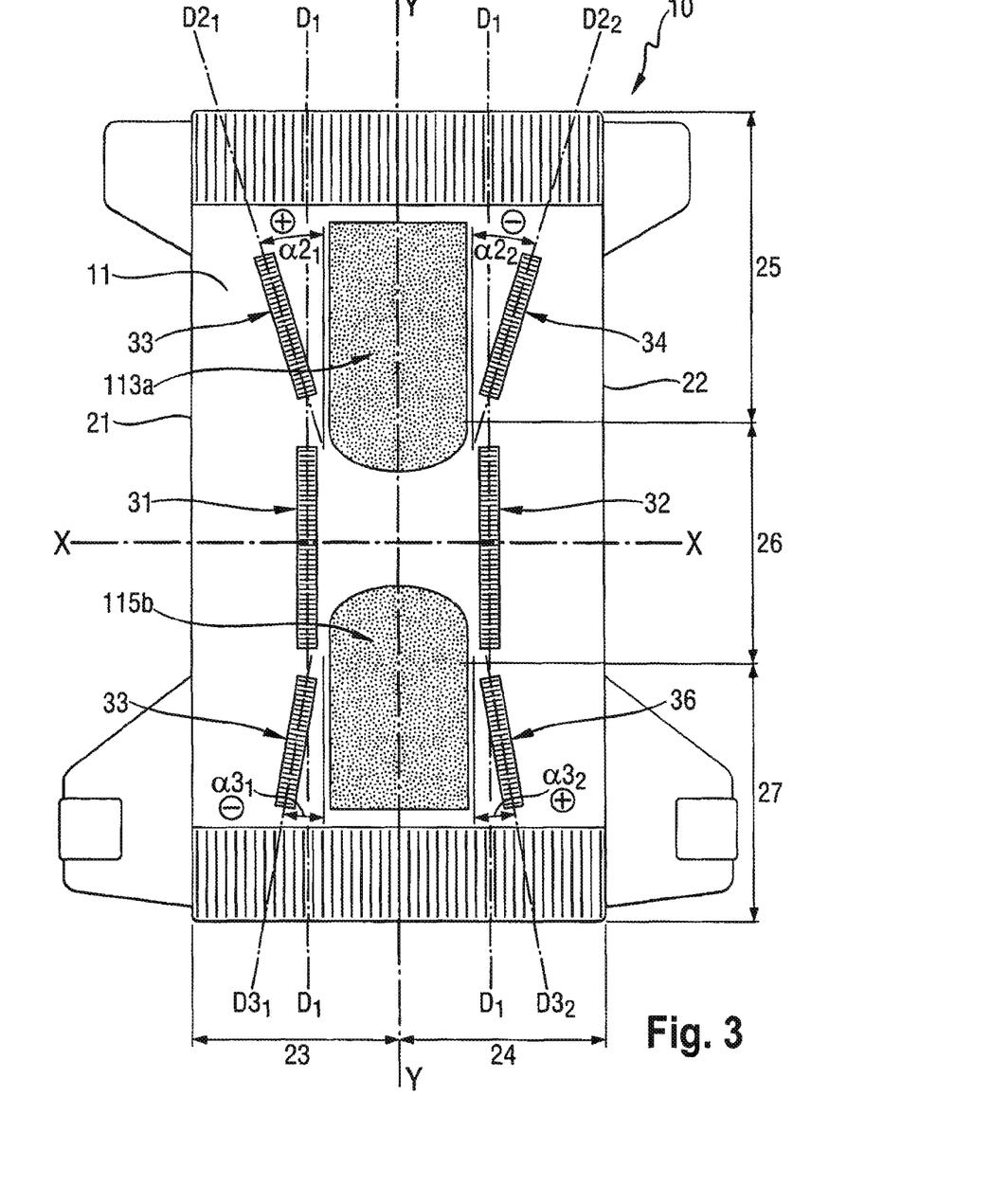
FIG. 3 shows a plan view of a disposable absorbent article configuration comprising two openings in the topsheet.

In another embodiment, the topsheet comprises more than one, for example may have two openings, as for example shown on FIG. 3. One of the openings (113a) may be present in at least part of the front portion (25) and may extend optionally into part of the crotch portion (26) of the topsheet (11). Another opening (113b) may be present in at least part of the back portion (27) and it may extend optionally into part of the crotch portion (26) of the topsheet (11).

When two or more openings are present, each opening may lead to the same or different void space. The article may comprise a transverse barrier that is positioned with a z-direction height (e.g., of at least 0.5 cm, or may be from 0.5 cm to 5 cm) substantially parallel to the transverse axis of the topsheet and between two openings. The transverse barrier may thus create two void spaces in the article.

It may be that the transverse barrier is attached to the topsheet.

In one embodiment, the article comprises two openings and two such void spaces, whereby one opening leads to one void space and one opening leads to another void space, the void spaces being separated from one another by such a transverse barrier.

The length of the openings, in the case of the topsheet comprises more than one opening is the sum of the longitudinal dimensions (length) substantially parallel to the longitudinal axis of the topsheet of each opening.

The maximum total length of the opening or openings may be for example 40% to 90% or may be 50% to 80%, or may be about 60% to 70%, of the total length L of the topsheet (in stretched state).

It may be that for size 4 diapers (with a maximum topsheet length of between 45 cm and 55 cm, typically between 48 cm and 52 cm), that the length of the opening or openings, when the diaper is in stretched state, is from 20 cm to 40 cm, or even from 25 cm to 35 cm, or even from 28 cm to 32 cm. It may be, for size 3 diapers (with a maximum topsheet length of between 40 cm and 50 cm, typically between 43 cm and 47 cm), that the length of the opening or openings, when the diaper is in stretched state, is from 17 cm to 37 cm, even from 22 cm to 32 cm, or even from 25 to 29 cm.

The average width of the opening or openings of the absorbent articles herein, in stretched state, may be from 5% to 30%, or may be 10% to 25%, or about 15% of the average width (including opening) of the topsheet, or for example (for a size 4 diaper), 15 mm to 60 mm, or may be from 20 mm to 50 mm.

In one embodiment, in particular when the topsheet comprises only a single opening, the longitudinal side edges of the opening are connected in the front and/or in the back by V-shaped edges, or rounded V-shaped edges (each of the V-shaped edges being two angled edges). This is further shown in FIG. 1, for example.

The topsheet comprises a first longitudinal side (23), positioned from the longitudinal axis (Y) to a first longitudinal side edge (21) and a second longitudinal side (24), positioned from the longitudinal axis (Y) to the opposite, second longitudinal side edge (22), as shown for example in FIG. 1.

Figure 2:
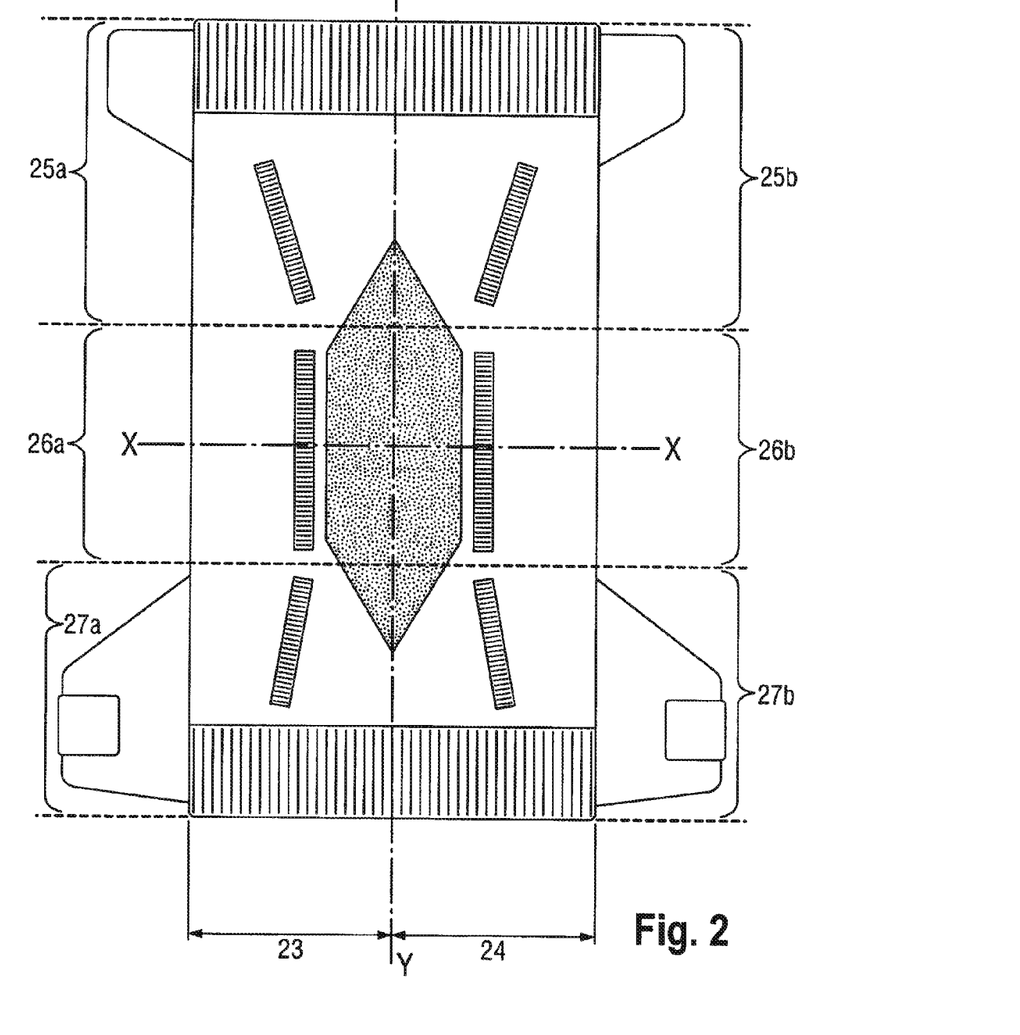
FIG. 2 shows a schematic plan view of a disposable absorbent article.

For the purpose of explanation, the topsheet may be divided into six portions, as exemplified in FIG. 2: the first longitudinal side (23) comprising a first front portion (25a), a first back portion (27a) and a first crotch portion (26a) positioned between the first front portion (25a) and the first back portion (27a) and the second longitudinal side (24) comprising a second front portion (25b), a second back portion (27b) and a second crotch portion (26b) positioned between the second front portion (25b) and the second back portion (27b).

As for example shown on FIGS. 1 and 3, the topsheet (11) of the absorbent article (10) comprises in at least part of the first crotch portion (26a), at least a first primary elasticated area (31) and in at least part of the second crotch portion (26b), at least a second primary elasticated area (32) and in at least part of the first front portion (25a), at least a first secondary elasticated area (33) and in at least part of the second front portion (25b), at least a second secondary elasticated area (34) and/or in at least part of the first back portion (27a), at least a first tertiary elasticated area (35) and in at least part of the second back portion (27b) at least a second tertiary elasticated area (36).

In one embodiment, the first crotch portion of the topsheet comprises only a single elasticated area and the second crotch portion comprises only a single elasticated area; and/or, the first front portion of the topsheet comprises only a single elasticated area and the second front portion comprises only a single elasticated area; and/or the first back portion of the topsheet comprises only a single elasticated area and the second back portion comprises only a single elasticated area.

In one embodiment, both the primary elasticated areas may have a greater elasticity than both the secondary and/or both the tertiary elasticated areas, e.g. an elasticity that is at least 20% more or at least 30% more (as % of stretched length at same force).

An elasticated area in the topsheet may be formed or applied by any method and in any form. In one embodiment herein, an elasticated area may be formed by the topsheet material and one or more bands of elastic material, e.g. an elastic band which has an average relaxed width of at least 3 mm, may be up to 30 mm and, may have a relaxed width to relaxed thickness ratio greater than 25 and less than 250, typically a single band.

Alternatively, an elasticated area may be formed from the topsheet material and a single strand or a multitude of strands of elastic material, each elastic strand having an average relaxed width of less than 3 mm, may be from 0.1 to 2.5 mm. It should be understood that in the case that an elasticated area is formed from the topsheet material and a multitude of elastic bands or strands, the elastic bands or strands in such an elasticated area are parallel to one another and the distance between neighboring elastic strands or bands in the area is less than 10 mm, may be less than 6 mm or less than 4 mm, in order to form a single elasticated area.

It may be that one or more elasticated areas comprise one or more elastic strands (may be one strand per area) and that one or more elasticated areas comprise one or more elastic bands (may be one band per area). In one embodiment, the primary elastic areas comprise each an elastic band and the secondary and or tertiary elasticated areas comprise each one or more elastic strands.

The topsheet (11) may comprise six elasticated areas, as shown on FIG. 1, each elasticated area comprising an elastic band. The six different elasticated areas provide a correct positioning and alignment of the opening (13), the two tertiary elasticated areas (35, 36) preventing moreover solid waste material from migrating into the back portion (27) of the topsheet (11). In another embodiment, the topsheet (11) may comprise two elastic bands in the crotch portion (26), each of which forming one primary elasticated area, and having two elastic strands in the front portion, each of which forming part of one secondary elasticated area and two elastic strands in the back portion, each of which forming part of one tertiary elasticated area, which together provide correct positioning and alignment of opening(s) in a cost-effective manner, as shown on FIG. 4.

In one embodiment, the topsheet (11) of the article has an elastic profile, based on a two-cycle hysteresis, measured by the ASTM 76-96 method, using a 500 mm/min clamp speed, as described in WO 03/009795, which is as follows:

1.5 Lt by a first load force of less than 1.1N, 3.0 Lt by a first load force of less than 2.1N and 4.5 Lt by a first load force of less than 3.0N and a second unload force at 4.5 Lt of more than 0.9N, a second unload force at 3.0 Lt of more than 0.5 and a second unload force at 1.5 Lt of more than 0.1N.

The profile of the topsheet may be:

1.5 Lt by a first load force of less than 0.6 N, 3.0 Lt by a first load force of less than 1.1N and 4.5 Lt by a first load force of less than 1.5N and a second unload force at 4.5 Lt of more than 0.9N, a second unload force at 3.0 Lt of more than 0.5N and a second unload force at 1.5 Lt of more than 0.1N.

Some profiles of the topsheet are defined by the first load force and second load forces at all of the lengths in the following table (for a two cycle hysteresis with 500 mm/min clamp speed, stretching as set out below, up to 4.5 Lt or $0.8 L_s$, which ever is smaller):

|  | One profile | Second profile | Third profile |
|---|---|---|---|
| $1^{st}$ load force at 1.5Lt | <1.1 N | <1.1 N | <0.6 N |
| $1^{st}$ load force at 2.0Lt | <1.5 N | <1.5 N | <0.8 N |
| $1^{st}$ load force at 2.5Lt * | <1.8 N | <1.8 N | <0.9 N |
| $1^{st}$ load force at 3.0Lt * | <2.1 N | <2.1 N | <1.1 N |
| $1^{st}$ load force at 3.5Lt * | <2.3 N | <2.3 N | <1.2 N |
| $1^{st}$ load force at 4.0Lt * | <2.6 N | <2.6 N | <1.3 N |
| $1^{st}$ load force at 4.5Lt * | <3.0 N | <3.0 N | <1.5 N |
| $2^{nd}$ unload force at 1.5Lt | >0.1 N | >0.2 N | >0.1 N |
| $2^{nd}$ unload force at 2.Lt | >0.3 N | >0.6 N | >0.3 N |
| $2^{nd}$ unload force at 2.5Lt * | >0.4 N | >0.8 N | >0.4 N |
| $2^{nd}$ unload force at 3.0Lt * | >0.5 N | >1.0 N | >0.5 N |
| $2^{nd}$ unload force at 3.5Lt * | >0.6 N | >1.2 N | >0.6 N |
| $2^{nd}$ unload force at 4.0Lt * | >0.7 N | >1.4 N | >0.7 N |
| $2^{nd}$ unload force at 4.5Lt * | >0.9 N | >1.8 N | >0.9 N |

* These values are only relevant as long as they are below $0.8L_s$, as mentioned in the test method (astm 76-96) disclosed in WO 03/009795.

In one embodiment, the absorbent article herein comprises a topsheet with an elasticated area comprising an elastic band, for example a primary elasticated area, and an elasticated area comprising a strand, for example a secondary and/or tertiary elasticated area, and the elasticated area comprising the band may have a greater unload force, as defined above, than the elasticated area comprising a strand, e.g. an unload force that is at least 20% more.

The first primary elasticated area and the second primary elasticated area have each a primary direction of stretch D1 substantially parallel to the longitudinal axis of the topsheet. The elasticated areas are typically straight and parallel to the longitudinal axis For example in the case of a topsheet comprising a single opening, as for example shown in FIG. 1, the first (31) and the second (32) primary elasticated areas may typically be spaced from the corresponding longitudinal side edge of the opening (14) with a transverse average distance of 0 to 10 or to 5 or to 3 mm. They may be parallel to the longitudinal side edges of the opening(s) (14).

The first (31) and second (32) primary elasticated areas are present in at least part of the crotch portion (26) of the topsheet (11) but they can extend from the crotch (26) to the front (25) and/or back portion (27) of the topsheet (11).

The width of the primary elasticated areas (31, 32) will vary, typically depending on the exact dimensions of the topsheet and/or the article, e.g. for example from 3 mm to 50 mm, or from 5 mm to 50 mm or to 20 mm.

For example, a primary elasticated area (31, 32), in stretched state, may be formed by the topsheet material and an elastic band, or a multitude of elastic strands, such that each elasticated area has an average relaxed width of about 3 mm to 50 mm, or 3 mm to 40 mm, or 3 mm to 20 mm, or 5 mm to 20 mm.

The first secondary elasticated area (33) has a direction of stretch $D2_1$, having an angle $\alpha2_1$ of 10 to 60°, or 15° to 45°, with a parallel line of D1; the second secondary elasticate area (34) has a direction of stretch $D2_2$, having an angle $\alpha2_2$ of −10° to −60°, or −15° to −45°, with a parallel line of D1.

The first (33) and second (34) secondary elasticated areas are present in the front portion (25) of the topsheet (11) but they may extend from the front portion (25) to (part of) the crotch portion (26).

The first tertiary elasticated area has a direction of stretch $D3_1$, having an angle $\alpha3_1$ of −10 to −60°, or −15° to −45°, with a parallel line of D1; the second tertiary elasticated area has a direction of stretch $D3_2$, having an angle $\alpha3_2$ of 10° to 60°, or 15° to 45°, with a parallel line of D1.

The first (35) and second (36) tertiary elasticated areas are present in the back portion (27) of the topsheet (11) but they may extend from the back portion (27) to (part of) the crotch portion (26).

The first primary elasticated area (31) and the first secondary elasticated area (33) and/or the first tertiary elasticated area (35) operate jointly to provide elasticity along the first longitudinal side (23) and the second primary elasticated area (32) and the second secondary elasticated area (34) and/or the second tertiary elasticated area (36) operate jointly to provide elasticity along the second longitudinal side. The different elasticated areas comprised by the first (23) and second longitudinal side (24) operate jointly to provide elasticity along the first (23) and the second longitudinal side (24) of the topsheet because each elasticated area provides elasticity along at least its length and the different elasticity's provided along the first (23) and the second longitudinal side (24) of the topsheet by each elasticated area contribute to provide an overall elasticity along the first (23) and the second longitudinal side (24) of the topsheet.

In one embodiment, the first primary elasticated area (31) and the first secondary elasticated area (33) may operate jointly to provide elasticity in a direction within 5 to 40° with a parallel line of the longitudinal axis of the topsheet and the second primary elasticated area (32) and the second secondary elasticated area (34) operate jointly to provide elasticity in a direction within −5 to −40° with a parallel line of the longitudinal axis of the topsheet and/or the first primary elasticated area (31) and the first tertiary elasticated area (35) operate jointly to provide an elasticity in a direction within −5 to −40° with a parallel line of the longitudinal axis of the topsheet and the second primary elasticated area (32) and the second tertiary elasticated area (36) operate jointly to provide an elasticity in a direction within 5 to 40° with a parallel line of the longitudinal axis of the topsheet.

In one embodiment, the total length of the elasticated areas comprised by one of the longitudinal sides of the topsheet is about 70% to 90%, or from about 75% to 85% of maximum length of the topsheet in a stretched state or at least 50% to at least 90% of the length of the opening (in a stretched state) or even beyond the opening in the case of the topsheet comprise only one opening.

A primary elasticated area is shaped such that it may be at least partially substantially parallel to the opposing primary elasticated area. Example lengths of the primary elasticated areas are about 30 to 60% of the maximum length of the topsheet in a stretched state.

The length of a secondary and/or tertiary elasticated area(s) will depend on the length of the article and the topsheet thereof. Example lengths of secondary and tertiary elasticated areas are about 10 to 30% of the maximum length of the topsheet in a stretched state.

The width of the secondary and/or tertiary elasticated area (s) on the topsheet will vary, typically depending on the exact dimensions of the topsheet and/or the article.

For example, for size 4 diapers as described above, a secondary and/or tertiary elasticated area(s), in stretched state, may be formed by the topsheet material and an elastic band, or a single strand or a multitude of elastic strands, such that each elasticated area has an average width of about 0.1 to 50 mm, or 3 mm to 40 mm, or 3 mm to 20 mm.

In one embodiment, as shown on the Figures, the primary, the secondary, and/or the tertiary elasticated areas may each independently, or all, be straight, which means that each elastic material comprised by an elasticated area has a linear orientation. In this case, the elastic areas are easily applied at high speed (e.g. since no diverging of elastics needs to take place).

Each elasticated area has on either side a transverse end edge (and thus each elasticated area comprising two transverse end edges). In one embodiment, the first end edge of the first primary elasticated area and an end edge of the first secondary elasticated area are in close proximity or contact with one another and the first end edge of the second primary elasticated area and an end edge of the second secondary elasticated area are in close proximity or contact with one another; and/or the second end edge of the first primary elasticated area and an end edge of the first tertiary elasticated area are in close proximity or contact with one another and the second end edge of the second primary elasticated area and an end edge of the second tertiary elasticated area are in close proximity or contact with one another. In one embodiment, for example when the elasticated areas are formed by attaching separate pieces of elastic material to a topsheet material, it may be beneficial from a process point of view that such transverse end edges are not in contact with one another.

In one other embodiment described in more detail below, the elasticated areas are formed by first joining (e.g. optionally via a carrier sheet) or attaching two or more, typically straight and optionally different, elastic materials to one another under an angle, e.g. those forming the first primary, secondary and/or tertiary areas, and then attaching the thus attached elastic materials to the topsheet material, and in such a case, the transverse edges of a first primary and a first secondary and/or the transverse edges of a first primary and a first secondary elasticated area are thus in contact with one another.

It may be beneficial from a performance point of view that they end edges are in close proximity or in contact with one another.

As used herein, the term 'in contact' means that one of the end edges of an elasticated area is directly touching one of the end edges of an other elasticated area (without any gap between the two end edges), but in one embodiment, may be without overlapping one another. As used herein, "in close proximity" means that the distance between one of the end edges of an elasticated area and one of the end edges of another elasticated area, as described above, is less than 4 cm, may be less than 3 cm or less than 2 cm (measured in stretch state).

In another embodiment, the first and second primary elasticated areas comprised by the topsheet are mirror images of another in the longitudinal axis, and the first and second secondary elasticated areas comprised by the topsheet are mirror images of another in the longitudinal axis and the first and second tertiary elasticated areas are mirror images of another in the longitudinal axis.

FIG. 1 is a plan view of an absorbent article (10) in its stretched state with the portion of the disposable absorbent article which contacts the wearer facing the viewer. The topsheet comprises an opening (13), the longitudinal side edges (14) of the opening being connected in the front and in the back by V-shaped edges, or rounded V-shaped edges (each of the V-shaped edges being two angled edges). The front V-shaped edges may have a larger angle than the back V-shape edges. The front V-shaped edges may have an angle of 20° to 140°, or from 45° to 65°, or from 55° to 60°, as described in WO 2006/031642. The topsheet (11) of the absorbent article (10) comprises in part of the first crotch portion (26a), a first primary elasticated area (31), in part of the second crotch portion (26b), a second primary elasticated area (32), in part of the first front portion (25a), a first secondary elasticated area (33), in part of the second front portion (25b), a second secondary elasticated area (34), in part of the first back portion (27a), a first tertiary elasticated area (35) and in part of the second back portion (27b) a second tertiary elasticated area (36), the different elasticated areas comprised by one of the longitudinal sides (23, 24) are in close proximity. Each elasticated area of an absorbent article may comprise an elastic band of L-89 elastic material, available from Fulflex, with (in relaxed state) a thickness of about 0.1 mm, a width of 20 mm.

FIG. 2 is a schematic plan view of an disposable absorbent article (10) in which for the purpose of explanation, the topsheet has been divided into six portions: the first longitudinal side (23) comprising a first front portion (25a), a first back portion (27a) and a first crotch portion (26a) positioned between the first front portion (25a) and the first back portion (27a) and the second longitudinal side (24) comprising a second front portion (25b), a second back portion (27b) and a second crotch portion (26b) positioned between the second front portion (25b) and the second back portion (27b), each portion of the topsheet comprising only one elasticated area formed by applying an elastic material which may be an elastic band to each of the six parts of the topsheet. The topsheet is such that the secondary and the tertiary elasticated areas do not cross or run parallel to the primary elasticated areas.

FIG. 3 is a plan view of an absorbent article (10) comprising two openings (115a, 115b). The topsheet (11) of the absorbent article (10) comprises in part of the first crotch portion (26a), a first primary elasticated area (31), in part of the second crotch portion (26b), a second primary elasticated area (32), in part of the first front portion (25a), a first secondary elasticated area (33), in part of the second front portion (25b), a second secondary elasticated area (34), in part of the first back portion (27a), a first tertiary elasticated area (35) and in part of the second back portion (27b) a second tertiary elasticated area (36), the different elasticated areas comprised by one of the longitudinal sides (23,24) are in close proximity. Each elasticated area comprises an elastic band.

Figure 4:
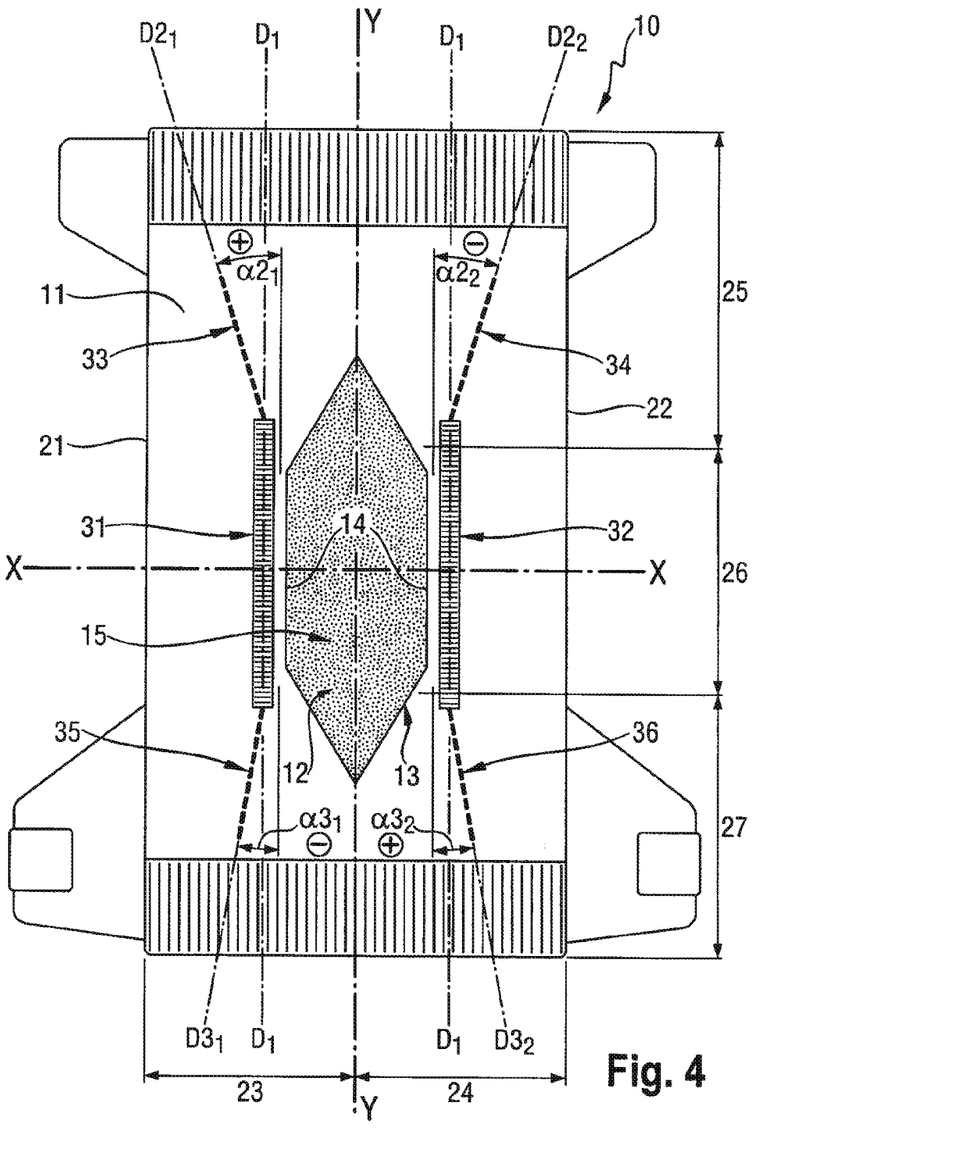
FIG. 4 shows a plan view of a disposable absorbent article configuration in which the secondary and the tertiary elasticated areas comprise an elastic strand.

FIG. 4 is a plan view of an absorbent article (10) comprising one opening (13). The first and second primary elasticated areas comprise an elastic band, the first and second secondary elasticated areas comprise an elastic strand and the first and second tertiary elasticated areas comprise an elastic strand. The different elasticated areas comprised by one of the longitudinal side are in contact with one another. They may be joined or attached to one another prior to attachment to the topsheet material, as described herein above and below.

In one embodiment herein the topsheet herein is such that the secondary elastics do not cross or run parallel to the primary elasticated areas and/or the tertiary elasticated areas do not cross or run parallel to the primary elasticated areas.

In one embodiment, the absorbent article is such that its topsheet has at no transverse cross section thereof comprising more than two elasticated areas.

In one embodiment, the elastics comprised by the first primary, the first secondary and the first tertiary elasticated areas are each straight, attached to one another under an angle before being applied to the topsheet material and the elastics comprised by the second primary, the second secondary and the second tertiary elasticated areas are each straight, attached to one another under an angle before being applied to the topsheet material.

As for example shown on FIG. 1, the described elasticated areas are such that on either longitudinal side of the topsheet the elasticated areas of that side do not run parallel or do not cross one another; and they may not overlap one another.

In an alternative embodiment, the first and second secondary elasticated areas and/or the first and second tertiary elasticated areas may have the same direction of stretch as the primary direction of stretch D1. The whole above description applies to this alternative embodiment except the description of angles $\alpha 2_1$, $\alpha 2_2$, $\alpha 3_1$ and $\alpha 3_2$.

The absorbent article may be sag-tolerable, and it thereto may have a topsheet that is sag-tolerable, as defined EP-A-1279388.

This means that the topsheet does not sag and that the topsheet keeps its z-direction alignment with the anal region and genitals of the wearer, and typically also its x and y direction alignment, when the backsheet and absorbent core sag due to increased weight of the body exudates received by the article. The absorbent article, which may be a diaper or training pants, has thereto means to ensure that the topsheet stays in about the same contact or close proximity with the wearer's anal and/or genital region when the backsheet and core sag, compared to just after application of the article to the wearer, when the backsheet and core do not yet sag. Typically the topsheet is sag-tolerable to such an extend that when the geometrical centre point of the backsheet is pulled down with 4 cm, the topsheet does not move down with more than 0.5 cm, or even not more than 0.25 cm, or typically the topsheet does not move down at all, and/or such that the longitudinal side edges of the opening do not move in the x and y direction with more than 0.5 cm, or may be not more than 0.25 cm, or does not move at all.

The longitudinal side edges of the topsheet may be joined or attached to the longitudinal side edges of the backsheet, by any attachment means known in the art, to form longitudinal opposing attachment areas. In one embodiment, the topsheet and the backsheet are attached directly to each other in some locations and are indirectly joined together in other locations.

The average width of the topsheet, including the width of the opening, may be larger than the average distance between the longitudinal attachment areas of the topsheet to the backsheet, mentioned above. Also it may be that the average width of the topsheet, including the width of the opening, is larger than the average width of the backsheet. The topsheet may for example have one or more transverse and/or longitudinal folds, which can unfold in use and allow sagging of the core and backsheet, while the topsheet remains in place.

The topsheet herein may be liquid or urine pervious or impervious. It may be that the topsheet is liquid or urine pervious in one direction, but liquid or urine impervious in the opposite direction, e.g. that body fluids may penetrate through the topsheet to the remaining part of the diaper, but that no or limited amounts of liquid (urine) can penetrate in reverse direction, towards the wearer's skin.

However, in one embodiment, the topsheet or at least more than 50% of its surface area (that faces the wearer in use) is hydrophobic. The topsheet may be urine impermeable and feces impermeable. Thereto, the topsheet is for example made of a material having a Strike Through time for the first gush of more than 120 seconds, as determined by the test method described hereinafter. Topsheets described herein are considered urine-impermeable and feces impermeable and thus suitable herein, when they have a low surface energy and a uniform pore size distribution, and have surface energy values, pore sizes and air permeability values described in EP-A-1417945. Materials may be used with an alcohol repellency of at least 7 or at least 8 or at least 9, or at least 10; and may have a surface energy of less than 25 mN/m; and may have a contact angle with water of above 130°; and may have a mean pore size of less than 20 microns, or less than 17 microns, or less than 13 microns, and may be at least 2 microns, or at least 5 microns. The topsheet may have an air permeability of at least 3 Darcy, or at least 10 Darcy, or at least 20 Darcy, or at least 30 Darcy, or 50 Darcy.

Thereto, topsheets may be made of hydrophobic material or are treated to be hydrophobic (in order to isolate the wearer's skin from liquids contained in remaining part of the diaper), with for example a hydrophobic surface coating. Example hydrophobic surface coatings are for example described in U.S. 60/543,785, filed Feb. 11, 2004. The hydrophobic surface coating may comprise one or more silicone polymers or fluorinated polymers A suitable topsheet may be manufactured from a wide range of materials, including woven or non-woven webs of natural fibers (e.g., wood or cotton fibers) or synthetic fibers (e.g., polyester, polyethylene and/or polypropylene fibers), or a combination of natural and synthetic fibers. If the topsheet includes fibers, the fibers may be for example spun bond, carded, wet-laid, melt blown, hydro entangled, or otherwise processed as is known in the art.

Materials may be compliant, soft feeling, and non-irritating to the wearer's skin.

Webs may include spunbond layers (S) and meltblown layer(s) (M), whereby the surfaces of the web are formed by spunbond layer(s). Webs may be used with a relatively high basis weight, for example 17 gram/$m^2$ or more, or for example 25 gram/$m^2$ (gsm) or more, or for example 34 gsm SMMS (whereby 12 gsm meltblown and 5 gsm spunbond); 34 gsm SMMS (whereby 10 gsm meltblown and 7 gsm spunbond);

30 gsm SMMS (whereby 10 gsm meltblown and 5 gsm spunbond); 30 gsm SMMS (whereby 8 gsm meltblown and 7 gsm spunbond); 34 gsm SMS (whereby 20 gsm meltblown and 7 gsm spunbond), ; the topsheet material may also comprise laminated layers or webs, comprising two or more SMS, SMMS and/or SMMS webs, as for example described above, e.g. for example a laminated web comprising two layers of 17 gsm SMMS, described above. (The elastic material may then be comprised between the webs.)

Any portion of the topsheet may be coated with a lotion or powder as is known in the art. Lotion may be present on the primary elasticated areas, and may be present on the secondary and/or tertiary elasticated areas. The lotion used on one elasticated area may be different to the lotion used on another elasticated area, or on the remaining part of the topsheet. Examples of lotions include those described in U.S. Pat. Nos. 5,607,760; 5,609,587; 5,635,191; 5,643,588; WO 95/24173, provided the lotion is compatible with the elastic material, and does not destroy the elastic material or reduce its elasticity.

The absorbent article may comprise a genital coversheet, which in use covers the genitals and protects the genitals from being soiled by feces. The genital coversheet may be present under, in or above the opening in the topsheet, typically only that part of the opening that is in close proximity with the genitals during use, i.e. the front region of the opening. The maximum length of the part of the genital coversheet that is present above, in or under the opening may be 10% to 50% of the maximum length of the opening(s), or 10% to 30%, or 13% to 28% or 17% to 27%. In some embodiments, at the most 50% of the maximum length of the opening(s) is 'covered' by the longest part of the genital coversheet, but at least 10% of the maximum length of the opening(s) is covered by the longest part of the genital coversheet.

The genital cover sheet may have a substantially transverse edge above, in or under the opening which is not straight, but may be curved or V-shaped (arrow shaped), having the centre point of the curved edge or of the V-shaped edge closer to the front of the article than the remaining part of the curved edge or V-shaped edge. Then, the length of the part of the genital coversheet from this centre point to the front of the opening may be 13% to 27% of the maximum length of the opening, or may be 15% to 20%.

When the genital coversheet may be present under the topsheet and below the opening, thus between the topsheet and the absorbent core, then, the genital coversheet is typically not attached to the absorbent core, to ensure the creation of a maximum void space for fecal material between the topsheet and the absorbent core and between the genital coversheet and the absorbent core.

The genital coversheet may be partially attached to the topsheet, forming hereby attachment areas and non-attached area(s), the latter being typically above, in or under the opening. The non-attached area(s) may then form the protective genital cover for the genitals, typically in the form of a pocket.

The genital coversheet may be urine permeable. Urine permeability can be determined by the Strike Through test, Edana test method 150.3-96, which is modified in that it applies 2 gushes of 5 ml at the same sample with a waiting time of 60 seconds between 2 gushes (without changing the absorbent pad) and in that the absorbent pad consists of 10 plies of filter paper, rather than 5 plies; the filter paper used may be Ahlstroem grade 989, or equivalent; the pick-up paper may be Ahlstroem Grade 632 or equivalent. This modified Edana test method provides the strike through times of the first gush and second gush, which are each an average of the values obtained in 3 tests.

Typically, the genital coversheet has an average urine permeability of the first gush strike through time of less than 7 seconds, or less than 5 seconds, or less than 3 seconds, and may be between 1 and 3 seconds or between 1 and 2 seconds. The genital coversheet may have a second gush strike through time of less than 9 seconds, or less than 7 seconds, or less than 5 seconds, and may be between 1 and 7 seconds or between 2 and 5 seconds.

The genital coversheet does not allow moisture to pass back to the skin, and thereto, it may have a low rewet. This can be determined by the Wetback Test, Edana test method 151.3-02, under 23° C. and 50% humidity test conditions, as specified in the Edana test, and using a filter paper with a loading factor of 3.30, as specified therein, and resulting in average rewet values, which are an average of 3 test results (the filter paper used may be as specified above). It may have an average rewet value of less than 0.8 g, less than 0.5 g, less than 0.3 g, or less than 0.2 g or even less than 0.15 g.

The absorbent article also comprises a, typically liquid impervious, backsheet, as known in the art. In some embodiments, the backsheet comprises a thin plastic film such as a thermoplastic film having a thickness of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE., and monolithic films such as manufactured by Clopay Corporation, Cincinnati, Ohio under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet may comprise elastomeric films, foams, strands, or combinations of these or other suitable materials with nonwovens or synthetic films.

The backsheet may be attached or joined to the topsheet, the absorbent core, or any other element of the diaper by any attachment means known in the art. It may be that the longitudinal side edges of the topsheet and backsheet are directly attached to one another, but that the longitudinal edges of the topsheet and the core are not attached to one another.

The attachment means to attach the topsheet and the backsheet, but also the genital coversheet herein may include a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core may comprise any absorbent material which is generally compressible, conformable, non-irritating to the wearer's skin, and capable of absorbing and retaining urine, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials; absorbent cores may have an absorbent storage layer which comprises more than 80% by weight of the absorbent core content (e.g. excluding core wrap) of absorbent gelling material, and which may be free of airfelt, i.e. 100% absorbent gelling material.

The absorbent article herein may be a disposable adult or infant diaper or training pants/ pull-up pants. Diapers or training pants may have side panels, and/ or more one or more pairs of elasticated leg cuffs that provide improved containment of liquids and other body exudates. Leg cuffs may also be referred to as leg bands, side flaps, barrier cuffs, or elastic cuffs, as described in; U.S. Pat. Nos. 3,860,003; 4,808,178; 4,695,278 and 4,795,454.

The diapers herein may have a fastening system, typically joined to the waistband, as known in the art. Some fastening systems comprise fastening tabs and landing zones, whereof the fastening tabs are attached or joined to the back region of the diaper and the landing zones are part of the front region of the diaper.

Processes to Make a Diaper

An article according to the present disclosure may be obtained by a process comprising the step of providing a topsheet material comprising a pair of opposing first and second longitudinal side edges, a longitudinal axis and a transverse axis, perpendicular to the longitudinal axis, a first longitudinal side, positioned from the longitudinal axis to a first longitudinal side edge of the topsheet comprising a first front portion, a first back portion and a first crotch portion positioned between the first front portion and the first back portion and a second longitudinal side positioned from the longitudinal axis to the opposite, second longitudinal side edge of the topsheet comprising a second front portion, a second back portion and a second crotch portion positioned between the second front portion and the second back portion.

A first primary elastic material is applied to at least part of the first crotch portion of the topsheet material, e.g. a nonwoven material, (and, when an opening is already present in the topsheet material, it may be for example spaced from the longitudinal side edge of the opening with a transverse distance of 0 to 10, or to 5, or to 3 mm) and a second primary elasticated material is applied to at least part of the second crotch portion of the topsheet, e.g. a nonwoven material, (and, when an opening is already present in the topsheet material, it may for example be spaced from the opposite longitudinal side edge of the opening with a transverse distance of 0 to 10 or to 5 or to 3 mm), such that a first primary elasticated area and a second primary elasticated area are obtained which extend along about the whole length of the opening(s).

The first and second primary elasticated areas extend in the crotch portion of the topsheet but they can extend in part of the front and/or the back portion of the topsheet.

The first and second primary elastic materials are applied to the topsheet having each a primary direction of stretch D1 substantially parallel to the longitudinal axis of the topsheet.

A first secondary elastic material is applied to at least part of the first front portion of the topsheet, e.g. a nonwoven material and a second secondary elasticated material is applied to at least part of the second front portion of the topsheet, e.g. a nonwoven material, such that a first secondary elasticated area and a second secondary elasticated area are obtained which extend in the front portion of the topsheet but they can extend from the front portion to the crotch portion of the topsheet. The first secondary elastic material is applied to the topsheet having a direction of stretch $D2_1$, having an angle $\alpha 2_1$ of 10 to 60° with a parallel line of D1 and the second secondary elastic material is applied to the topsheet having a direction of stretch $D2_2$, having an angle $\alpha 2_2$ of −10° to −60° with a parallel line of D1.

A first tertiary elastic material is applied to at least part of the first back portion of the topsheet, e.g. a nonwoven material and a second tertiary elastic material is applied to at least part of the second back portion of the topsheet, e.g. a nonwoven material, such that a first tertiary elasticated area and a second tertiary elasticated area are obtained which may extend in the back portion of the topsheet but they can extend in a part of the crotch portion of the topsheet. The first tertiary elastic material is applied to the topsheet having a direction of stretch $D3_1$, having an angle $\alpha 3_1$ of −10 to −60° with a parallel line of D1 and the second tertiary elastic material is applied to the topsheet having a direction of stretch $D3_2$, having an angle $\alpha 3_2$ of 10° to 60° with a parallel line of D1.

The primary, the secondary and the tertiary elasticated materials may, each independently, be applied directly to the topsheet material e.g. in stretched or partially stretched state, i.e. to the top surface or bottom surface of the topsheet, or they may, each independently, be indirectly applied e.g. in stretched or partially stretched state to the topsheet, e.g. by first applying one or more elastic areas to a carrier material and applying the carrier material to the topsheet material. They may be applied such that they are not in direct contact with the skin of the user, e.g. applied to the bottom of the topsheet material, not facing the user in use, or applied to the top of the topsheet material and covered with a covering strip (which may be the carrier material).

In one embodiment, one or more or all of the elastic materials are attached to a carrier sheet first, for example such that the transverse edges are not in contact with one another or such that they are in contact with one another, as described above, and then the carrier sheet is attached to the topsheet material. The carrier sheet and topsheet may be joined such that the elastic materials are positioned between the carrier sheet and topsheet material.

In one embodiment, the first primary, the first secondary and/or the first tertiary elastic materials, that are typically straight, are attached to one another under an angle, such as defined herein, before being applied directly or indirectly to the topsheet material; and the second primary, the second secondary and the second tertiary elastic materials are each straight, attached to one another under an angle before being applied directly or indirectly to the topsheet material. Optionally, the thus attached elastic material may be attached to a carrier sheet, and then attached to the topsheet material.

An elasticated area herein may comprise (a multitude of) elastic strands or bands or in one embodiment, as single elastic band, each band or strand having an average thickness (e.g. gauge) of at least 20 microns, or at least 40 microns, or at least 60 microns, typically up to about 300 microns, or up to 200 microns or up to 150 microns. Some materials have an average thickness of about 70 to 100 microns and a relaxed width to relaxed thickness ratio greater than 25 and less than 250.

Elastic band materials used hereto may include VFE-CD, available from Tredegar, and L-86, L-89, or L-90, available from Fulflex (Limerick, Ireland). Elastic strand material includes Lycra and equivalents, as for example available from Du Pont Nemours.

It may be that the elasticated areas comprise elastic material adhered to the topsheet material by a bonding technique, such as ultrasonic bonding, thermal bonding, or adhesive bonding. Some adhesives for attaching the primary, secondary and tertiary elastic strands or bands include D3166 ZP, available from H.B. Fuller (St Pauls, USA) and H2401, available from Bostik. Each elastic band or strand may be glued in a stretched or partially stretched state to the topsheet material or a carrier material.

Longitudinally extending (slit) opening or openings may be formed (cut) in the topsheet material first prior to forming the elasticated area(s). Alternatively, the primary elastic bands or strands, the secondary elastic bands or strands and the elasticated areas are first formed, e.g. by applying elastic material to the topsheet material, e.g. in stretched or partially stretched state, whereafter one or more longitudinally extending (slit) opening(s) is or are formed (cut) through part of the topsheet material, typically along at least part of the longitudinal axis of the topsheet material.

In one embodiment, an opening with a length in a stretched state of between 20 cm and 40 cm, typically about 25 cm to 35 cm is cut in the nonwoven. This may be cut as a slit, whereby the slit opening obtains its width due to the spreading elasticated areas, or the slit opening may be cut with a width dimension, for example up to 5.0 cm. (As mentioned above, if the elastic areas are present on the surface of the topsheet which is in contact with the skin of the user, it may be that an additional layer, a so-called covering strip, e.g. nonwoven material, is placed on the elastic areas, to avoid direct contact by the elastic areas with the skin; this covering strip may be the carrier sheet described above). The topsheet may be used on a Pampers Premium Size 4 diaper, designed for a baby weight range of 21-37 pounds or on a Pampers Premium Size 3 diaper. It may also replace the layer of a Pampers Premium Size 3 or 4, which is on the absorbent core and in use in contact with the skin of the baby. Thereto, the topsheet with the elastic bands are attached to the front and back waistbands, and typically to the longitudinal side edges of the backsheet.

The dimensions and other parameters of the exemplary diaper embodiments described above can be readily modified by one skilled in the art to smaller or larger wearers, including adult wearers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A disposable absorbent article having a backsheet, a topsheet and an absorbent core, the absorbent core positioned between the topsheet and the backsheet, the topsheet comprising:
   a pair of opposing first and second longitudinal side edges;
   a longitudinal axis and a transverse axis perpendicular to the longitudinal axis;
   a first longitudinal side, positioned from the longitudinal axis to a first longitudinal side edge of the topsheet, the first longitudinal side comprising a first front portion, a first back portion, and a first crotch portion positioned between the first front portion and the first back portion;
   a second longitudinal side positioned from the longitudinal axis to the second longitudinal side edge of the topsheet, the second longitudinal side comprising a second front portion, a second back portion and a second crotch portion positioned between the second front portion and the second back portion;
   an opening having first and second opposing longitudinal side edges, and providing a passageway to a void space for receiving bodily exudates therein, the void space positioned between the topsheet and the absorbent core;
   a first primary elasticated area in the first crotch portion and a second primary elasticated area in the second crotch portion, the first elasticated area and the second primary elasticated area having each a primary direction of stretch D1 substantially parallel to the longitudinal axis of the topsheet, wherein the first primary elasticated area and the second primary elasticated area each include a first transverse end edge and a second transverse end edge;
   a first secondary elasticated area in the first front portion, the first secondary elasticated area having a direction of stretch $D2_1$, having an angle $\alpha 2_1$ of 10 to 60° with a parallel line of D1, wherein the first secondary elasticated area includes a first transverse end edge and a second transverse end edge;
   a second secondary elasticated area in the second front portion, the second secondary elasticated area having a direction of stretch $D2_2$, having an angle $\alpha 2_2$ of −10° to −60° with a parallel line of D1, wherein the second secondary elasticated area includes a first transverse end edge and a second transverse end edge;
   a first tertiary elasticated area in at least part of the first back portion, the first tertiary elasticated area having a direction of stretch $D3_1$, having an angle $\alpha 3_1$ of −10 to −60° with a parallel line of D1, wherein the first tertiary elasticated area includes a first transverse end edge and a second transverse end edge; and
   a second tertiary elasticated area in the second back portion, the second tertiary elasticated area having a direction of stretch $D3_2$, having an angle $\alpha 3_2$ of 10° to 60° with a parallel line of D1, wherein the second tertiary elasticated area includes a first transverse end edge and a second transverse end edge, wherein the first primary elasticated area is longitudinally spaced apart from the first secondary elasticated area;

wherein the second primary elasticated area is longitudinally spaced apart from the second secondary elasticated area;

wherein the first primary elasticated area is longitudinally spaced apart from the first tertiary elasticated area; and wherein the second primary elasticated area is longitudinally spaced apart from the secondary tertiary elasticated area.

2. The disposable absorbent article according to claim 1, wherein the first primary elasticated area, the first secondary elasticated area, and the first tertiary elasticated area operate jointly to provide elasticity along the first longitudinal side, and wherein the second primary elasticated area, the second secondary elasticated area, and the second tertiary elasticated area operate jointly to provide elasticity along the second longitudinal side.

3. The disposable absorbent article according to claim 1, wherein:

the first primary elasticated area and the first secondary elasticated area operate jointly to provide a elasticity in a direction within 5 to 40° with a parallel line of the longitudinal axis of the topsheet and wherein the second primary elasticated area and the second secondary elasticated area operate jointly to provide elasticity in a direction within −5 to −40° with a parallel line of the longitudinal axis of the topsheet; and the first primary elasticated area and the first tertiary elasticated area operate jointly to provide a elasticity in a direction within −5 to −40° with a parallel line of the longitudinal axis of the topsheet and wherein the second primary elasticated area and the second tertiary elasticated area operate jointly to provide elasticity in a direction within 5 to 40° with a parallel line of the longitudinal axis of the topsheet.

4. The disposable absorbent article according to claim 1, wherein the primary, the secondary, and the tertiary elasticated areas are each straight.

5. The disposable absorbent article according to claim 4, wherein the first and second primary elasticated areas are mirror images of each other with respect to the longitudinal axis, wherein the first and second secondary elasticated areas are mirror images of each other with respect to the longitudinal axis, and wherein the first and second tertiary elasticated areas are mirror images of each other with respect to the longitudinal axis.

6. The disposable absorbent article according to claim 4, wherein the first secondary and the second tertiary elasticated areas define an angle of from 15° to 45° with a parallel line of D1 and wherein the second secondary and the first tertiary elasticated areas define an angle of from −15° to −45° with a parallel line of D1.

7. The disposable absorbent article according to claim 1, wherein the primary, the secondary, and the tertiary elasticated areas each comprise an elastic band having an average width of at least 3 mm and up to 30 mm and a relaxed width to relaxed thickness ratio greater than 25 and less than 250.

8. The disposable absorbent article according to claim 1, wherein the primary, the secondary, and the tertiary elasticated areas each comprise elastics strands, each strand having an average width of less than 3 mm, and wherein a distance between neighboring elastic strands in each area is less than 4 mm.

9. The disposable absorbent article according to claim 1, wherein the primary elasticated areas each comprise an elastic band, and wherein both the secondary and the tertiary elasticated areas each comprise an elastic strand.

10. A disposable absorbent article having a backsheet, a topsheet and an absorbent core, the absorbent core being positioned between the topsheet and the backsheet, the topsheet comprising:

a pair of opposing first and second longitudinal side edges;

a longitudinal axis and a transverse axis perpendicular to the longitudinal axis;

a first longitudinal side, positioned from the longitudinal axis to a first longitudinal side edge of the topsheet, the first longitudinal side comprising a first front portion, a first back portion, and a first crotch portion positioned between the first front portion and the first back portion;

a second longitudinal side positioned from the longitudinal axis to the second longitudinal side edge of the topsheet, the second longitudinal side comprising a second front portion, a second back portion, and a second crotch portion positioned between the second front portion and the second back portion;

an opening having first and second opposing, longitudinal side edges, and providing a passageway to a void space for receiving bodily exudates therein, the void space positioned between the topsheet and the absorbent core;

a first primary elasticated area in the first crotch portion and a second primary elasticated area of the second crotch portion, each elasticated area having each a primary direction of stretch D1 substantially parallel to the longitudinal axis of the topsheet wherein the first primary elasticated area and the second primary elasticated area each include a first transverse end edge and a second transverse end edge; and a first secondary elasticated area in the first front portion and a second secondary elasticated area in the second front portion, each elasticated area having the same direction of stretch as the primary direction of stretch, wherein the first secondary elasticated area and the second secondary elasticated area each include a first transverse end edge and a second transverse end edge; and a first tertiary elasticated area in the first back portion and a second tertiary elasticated area in second back portion, each elasticated area having the same direction of stretch as the primary direction of stretch, wherein the first tertiary elasticated area and the second tertiary elasticated area each include a first transverse end edge and a second transverse end edge, wherein the first primary elasticated area is longitudinally spaced apart from the first secondary elasticated area;

wherein the second primary elasticated area is longitudinally spaced apart from the second secondary elasticated area;

wherein the first primary elasticated area is longitudinally spaced apart from the first tertiary elasticated area; and wherein the second primary elasticated area is longitudinally spaced apart from the secondary tertiary elasticated area.

11. A method for making a topsheet for a disposable absorbent article, the method comprising the steps of:

a) providing a topsheet material comprising:

i. a pair of opposing first and second longitudinal side edges;

ii. a longitudinal axis and a transverse axis perpendicular to the longitudinal axis;

iii. a first longitudinal side positioned from the longitudinal axis to a first longitudinal side edge, the first longitudinal side comprising a first front portion, a first back portion, and a first crotch portion positioned between the first front portion and the first back portion; and iv. a second longitudinal side positioned from the longitudinal axis to the second longitudinal side edge, the second longitudinal side comprising a second front portion, a second back portion, and a second crotch portion positioned between the second front portion and the second back portion; and b) providing a multitude of elastic materials; and applying a first primary elastic material to the first crotch portion and applying a second primary elastic material the second crotch portion, the first primary elastic material defining a first primary elasticated area in the first crotch portion and the second primary elastic material defining a second primary elasticated area in the second crotch portion, the first elasticated area and the second primary elasticated area having each a primary direction of stretch D1 substantially parallel to the longitudinal axis, wherein the first primary elasticated area and the second primary elasticated area each include a first transverse end edge and a second transverse end edge;

c) applying a first secondary elastic material to the first front portion and applying a second secondary elastic material to the second front portion, the first secondary elastic material defining a first secondary elasticated area in the first front portion, the first secondary elasticated area having a direction of stretch $D2_1$, having an angle $\alpha2_1$ of 10 to 60° with a parallel line of D1, and the secondary elastic material defining a second secondary elasticated area in the second front portion, the second secondary elasticated area having a direction of stretch $D2_2$, having an angle $\alpha2_2$ of −10° to −60° with a parallel line of D1, wherein the first secondary elasticated area and the second secondary elasticated area each include a first transverse end edge and a second transverse end edge; and d) applying a first tertiary elastic material to the first back portion and applying a second tertiary elastic material to the second back portion, wherein the first tertiary elastic material defines a first tertiary elasticated area in at least part of the first back portion, the first tertiary elasticated area having a direction of stretch $D3_1$, having an angle $\alpha3_1$ of −10 to −60° with a parallel line of D1, and wherein the second tertiary elastic material defines a second tertiary elasticated area in the second back portion, the second tertiary elasticated area having a direction of stretch $D3_2$, having an angle $\alpha3_2$ of 10° to 60° with a parallel line of D1 wherein the first tertiary elasticated area and the second tertiary elasticated area each include a first transverse end edge and a second transverse end edge, wherein the first primary elasticated area is longitudinally spaced apart from the first secondary elasticated area;

wherein the second primary elasticated area is longitudinally spaced apart from the second secondary elasticated area;

wherein the first primary elasticated area is longitudinally spaced apart from the first tertiary elasticated area; and wherein the second primary elasticated area is longitudinally spaced apart from the secondary tertiary elasticated area.

12. The process according to claim 11, further comprising the step of forming an opening in the topsheet material along the longitudinal axis, the opening having first and second opposing longitudinal side edges.

13. A process according to claim 12, whereby the elastic materials are each applied in a stretched state.

* * * * *